US012262764B2

(12) United States Patent
Rahimi (10) Patent No.: US 12,262,764 B2
(45) Date of Patent: Apr. 1, 2025

(54) HYGIENE DEVICE, IN PARTICULAR A RESPIRATORY PROTECTION MASK

(71) Applicants: Alireza Rahimi, Ratingen (DE); Sholeh Rahimi, El Dorado Hills, CA (US); Albert Seena Nasr, El Dorado Hills, CA (US)

(72) Inventor: Alireza Rahimi, Ratingen (DE)

(73) Assignees: Alireza Rahimi, Ratingen (DE); Sholeh Rahimi, El Dorado Hills, CA (US); Albert Seena Nasr, El Dorado Hills, CA (US)

( * ) Notice: Subject to any disclaimer, the term of this patent is extended or adjusted under 35 U.S.C. 154(b) by 361 days.

(21) Appl. No.: 17/471,404

(22) Filed: Sep. 10, 2021

(65) Prior Publication Data

US 2022/0079254 A1 Mar. 17, 2022

(30) Foreign Application Priority Data

Sep. 11, 2020 (DE) ...................... 10 2020 123 765.0
Feb. 4, 2021 (DE) ...................... 10 2021 102 650.4

(51) Int. Cl.
*A41D 13/11* (2006.01)
*A01K 1/01* (2006.01)
(Continued)

(52) U.S. Cl.
CPC ............ *A41D 1/002* (2013.01); *A01K 1/0107* (2013.01); *A41D 13/1161* (2013.01);
(Continued)

(58) Field of Classification Search
CPC ...... A01K 1/0107; A41D 1/002; A41D 13/11; A41D 13/1161; A41D 13/1184;
(Continued)

(56) References Cited

U.S. PATENT DOCUMENTS 4,796,014 A * 1/1989 Chia .................... A61F 5/48
340/573.5
6,200,250 B1 * 3/2001 Janszen ................. A61F 13/42
493/938

(Continued)

FOREIGN PATENT DOCUMENTS

CA 2615541 A1 * 6/2008 ....... A61F 13/55175
JP 2004139545 A * 5/2004 ............. G06F 17/60
JP 6425266 B2 11/2018

*Primary Examiner* — Stephen R Burgdorf
(74) *Attorney, Agent, or Firm* — Rankin, Hill & Clark LLP (57) ABSTRACT

The invention relates to a hygiene device, having a material body, which covers a region in the intended positioned state, and in particular has multiple plies (a, b, c) of material, in particular moisture absorption material, which is made of a plastic material, wood, paper, and/or granular material, wherein the hygiene device has at least one sensor (4) for measuring a parameter. It is proposed that the hygiene device has at least one transmitter module (5) on or in the material of the material body, the at least one sensor (4) is integrated in the transmitter module (5), and the transmitter module (5) is designed for the contactless transmission of sensor data of the at least one sensor (4) and without its own electrical energy source.

22 Claims, 3 Drawing Sheets (51) Int. Cl.
*A41D 1/00* (2018.01)
*A62B 18/02* (2006.01)
*G08B 7/06* (2006.01)
*G08B 21/18* (2006.01)
*H04B 1/3827* (2015.01)
*H04W 4/80* (2018.01)

(52) U.S. Cl.
CPC ............... *A62B 18/02* (2013.01); *G08B 7/06* (2013.01); *G08B 21/182* (2013.01); *H04B 1/385* (2013.01); *H04B 2001/3866* (2013.01); *H04W 4/80* (2018.02)

(58) Field of Classification Search
CPC .. A47K 5/1211; A47K 5/1217; A61B 5/0002; A61B 5/01; A61B 5/0205; A61B 5/082; A61B 5/14539; A61B 5/6803; A61B 5/7475; A61B 2560/0214; A61B 2562/029; A61F 13/42; A61L 9/00; A61M 16/142; A62B 18/02; A62B 18/025; A62B 23/025; G08B 7/06; G08B 21/182; G08B 21/245; H04B 1/385; H04B 2001/3866; H04M 1/72412; H04W 4/80
USPC ........................................................ 340/500
See application file for complete search history.

(56) References Cited

U.S. PATENT DOCUMENTS

| | | | |
|---|---|---|---|
| 10,772,287 B1* | 9/2020 | Van Eeden | A01K 1/011 |
| 2003/0006244 A1* | 1/2003 | Silvers | B65F 1/06 |
| | | | 221/97 |
| 2004/0220538 A1* | 11/2004 | Panopoulos | A61F 13/42 |
| | | | 604/361 |
| 2012/0313786 A1* | 12/2012 | Clary | A01K 1/0107 |
| | | | 340/573.3 |
| 2014/0375428 A1* | 12/2014 | Park | G06K 19/0716 |
| | | | 340/10.1 |
| 2015/0150732 A1* | 6/2015 | Abir | A61F 5/48 |
| | | | 356/445 |
| 2018/0049926 A1* | 2/2018 | Lin Charna | H04B 1/3888 |
| 2019/0228640 A1* | 7/2019 | Freedman | G08B 21/18 |
| 2019/0314214 A1* | 10/2019 | Halvorsen | A61F 13/42 |
| 2020/0114178 A1* | 4/2020 | Waterford | A62B 23/02 |
| 2021/0386142 A1* | 12/2021 | Doyle | A62B 23/025 |
| 2021/0397213 A1* | 12/2021 | Kariguddaiah | A61B 5/02438 |
| 2022/0168154 A1* | 6/2022 | Dean | A61F 13/42 |
| 2022/0168155 A1* | 6/2022 | Webb | G08B 21/02 |
| 2022/0233363 A1* | 7/2022 | Heirman | A61F 13/42 |
| 2023/0290476 A1* | 9/2023 | Gylleby | A61B 50/30 |
| | | | 235/492 |

* cited by examiner

HYGIENE DEVICE, IN PARTICULAR A RESPIRATORY PROTECTION MASK

The invention relates to a hygiene device, a transmitter module for a hygiene device, an indicator module for a hygiene device, a monitoring arrangement that includes a hygiene device, a return arrangement for a hygiene device, and a respiratory mask.

The hygiene device mentioned is used in particular as a respiratory mask in the scope of preventive measures for protection from infections by secretion droplets having pathogens, in particular bacteria and viruses. Another example is an application in the scope of hygienic care of humans and animals, in particular for the hygienic absorption of excretions.

The known hygiene device in the form of a respiratory mask (JP 642566 B2), from which the invention starts, is equipped with a shaping metal part as a nose clip and an electronic circuit module on the mask body for measuring biosignals and transferring them to a management server or the like. The electronic circuit module has a sensor, a wireless communication unit electrically connected to the sensor, and an antenna terminal electrically connected to the wireless communication unit. The antenna terminal is electrically connected to the shaping metal part, due to which the metal part is additionally used as an antenna via which sensor data are wirelessly transmitted by the communication unit for information management to the management server. The electronic circuit module is equipped with a battery as an electrical energy source for the power supply of the components of the known respiratory mask required for the intended function.

As a result, the known respiratory mask is linked to a high level of electronic complexity and an accompanying occurrence of electrical signals. Very generally, the known respiratory mask has a complex electronic structure.

The invention is based on the problem of designing and refining the known hygiene device in such a way that the structural design of the hygiene device, in particular the electronic complexity, is further simplified without otherwise impairing the performance.

The above problem is achieved in a hygiene device as disclosed and claimed herein.

The fundamental consideration is essentially that the hygiene device, which is in particular a respiratory mask, does have at least one transmitter module and at least one sensor, but does not necessarily have to be equipped with its own energy source for the power supply of the electronic components required for the intended function. Rather, it has been recognized that with suitable electronic design, the electronic complexity can be reduced and a separate electrical energy source is not necessary. Negative effects due to electrical interference signals on electronic devices located in the environment can thus be minimized without otherwise impairing the performance. It is particularly to be emphasized in the case of a respiratory mask as the hygiene device that the sensor data can subsequently be used to determine the wearing time of the respective respiratory mask and to be able to better estimate an accompanying contamination risk and to avoid a respiratory mask waste.

The special design of the proposed hygiene device furthermore has the advantage that the electronic components are designed modularly and therefore particularly compactly, which is accompanied per se by a reduction of the electronic complexity, the required installation space, and the resulting weight.

Specifically, it is proposed that the hygiene device has at least one transmitter module on or in the material of the material body, the at least one sensor is integrated into the transmitter module, and the transmitter module is designed for the contactless transmission of sensor data of the at least one sensor and without its own electrical energy source.

According to a particularly preferred embodiment, the hygiene device is a respiratory mask, having a mask body covering the mouth and nose of a user in the intended applied state, which forms the material body, having fixing elements fastened on the mask body, in particular fastening bands, configured for fixing the mask body on the head of the user, wherein the respiratory mask has the at least one transmitter module on or in the material of the mask body. This offers optimum protection from infections by secretion droplets. The hygiene device can also be designed in another way, for example, as an animal toilet device.

According to a likewise preferred embodiment, the at least one sensor can be configured to make a contamination state of the hygiene device based on the measured parameter derivable. This enables a qualitative estimation of the contamination state of the proposed hygiene device.

According to a particularly preferred embodiment, the at least one transmitter module can be designed as an RFID module and/or as an NFC module. The design as an RFID and/or NFC module offers the advantages of a small size, low electronic complexity, inconspicuous readout options, and low costs of the RFID and/or NFC components required for the intended function.

According to a preferred embodiment, the at least one transmitter module can be designed to be wireless. This preferred embodiment enables a particularly advantageous and compact construction, which therefore saves installation space.

According to a likewise preferred embodiment, the at least one transmitter module has a carrier component on which the at least one sensor and at least one further component of the transmitter module required for the intended function are fixed relative to one another and thus form an assembly unit. This assembly unit represents an assembly which can be handled as such in the context of assembly of the proposed hygiene device, which enables a particularly high level of design flexibility.

According to a further preferred embodiment, the transmitter module is fastened fixed in place on or in the material body, in particular the mask body. No additional aids are thus necessary. Alternatively, the at least one transmitter module can be arranged loosely on the material body.

According to a further preferred embodiment, the transmitter module is fastened captively on or in the material body, in particular the mask body. In particular, this prevents a nondestructive detachment of the transmitter module from the mask body. However, a nondestructive detachment of the captively fastened transmitter module from the mask body is also conceivable in principle in an alternative embodiment.

The further preferred embodiment shows that the proposed solution permits a high level of design flexibility. This is expressed here in that precisely one transmitter module can be designed having precisely one or multiple sensors or multiple transmitter modules can be designed each having precisely one or each having multiple sensors. This offers the advantage that the design of the proposed hygiene device can be adapted to individual requirements with respect to the complexity of the hygiene device as such and the number of the sensors.

The further preferred embodiment relates to the type of the sensor parameters. The large number of the measurable parameters enables special flexibility with respect to the application.

The further preferred embodiment relates to the measurement of the sensor parameters. The parameters measured by the sensor are based here either on measurement data of the respective hygiene device user or on measurement data of the environment of the proposed hygiene device. Such measurement data thus ultimately enable a more accurate estimation of demand for the proposed hygiene device and therefore reduce the premature replacement and the accompanying costs.

According to a particularly preferred embodiment, the hygiene device is designed as a single-use or multiple-use product. This enables greater flexibility with respect to the use and design of the hygiene device.

According to the preferred embodiments, a corresponding receiver module is associated with the transmitter module, with which it interacts and forms a transmitter-receiver system. In this case, exclusively the receiver module activates the transmitter module and supplies it with energy. This embodiment offers the advantage that the transmitter module of the proposed hygiene device is a passive module without its own power supply. An electromagnetic field into which the transmitter module can transmit the sensor data only becomes active originating from the corresponding receiver module. This offers the advantage that the proposed hygiene device can be used at locations having devices sensitive to electromagnetic signals. Interferences of electrical devices are minimized by this particularly preferred embodiment and a strain of the environment by electrical signals is fundamentally reduced.

According to a particularly preferred embodiment, the interaction of the transmitter-receiver system required for the intended function can be carried out up to a range of at least 3 m. This opens up a particular level of flexibility with respect to the usage options of the proposed hygiene device, since greater maximum distances between transmitter and receiver are thus enabled.

According to a further teaching, which has independent significance, a hygiene device, in particular a proposed hygiene device according to the above teaching, is disclosed having a material body, which covers a region in the state positioned as intended, and in particular has multiple plies of material, in particular moisture absorption material, which is made of a plastic material, wood, paper, and/or granular material, in particular a mask body. This is particularly preferably a respiratory mask having a mask body, which covers the mouth and nose of a user in the state applied as intended, and in particular has multiple plies of material, having fixing elements fastened on the mask body, in particular fastening bands, configured for fixing the mask body on the head of the user. In this case, the hygiene device, in particular the respiratory mask, has at least one pH and/or moisture indicator on or in the material of the material body, in particular the mask body. This indicator can also be part of an indicator module described hereinafter. Reference can thus be made in this regard to all statements on the proposed hygiene device according to the first teaching.

It is particularly to be emphasized that the indicator, which colors accordingly with changing, in particular rising or sinking pH value and/or with rising moisture, can be used for the indication to determine the wearing time of the respective hygiene device and to be able to better estimate an accompanying contamination risk and to avoid a hygiene device waste.

Also disclosed is a buffer arrangement, which is configured to absorb moisture, in particular from the respiratory air and/or from the environment, and deliver it with a time delay to the sensor and/or indicator. One advantage of this is that an essentially constant and continuous measurement over a specific time period is enabled using the sensor or that the indication of pH value and/or moisture changes essentially constantly and continuously.

According to a further teaching, which also has independent significance, a transmitter module for a proposed hygiene device is disclosed, wherein the transmitter module has a carrier component, on which the at least one sensor and at least one further component of the transmitter module required for the intended function, preferably the microchip and/or the antenna, furthermore preferably all components of the at least one transmitter module required for the intended function are fixed relative to one another and thus form an assembly unit, which is arrangeable as a whole on or in the material of the material body. Reference can be made in this regard to all statements on the proposed hygiene device according to the first and second teaching.

According to a further teaching, which also has independent significance, an indicator module for a proposed hygiene device is disclosed, wherein the indicator module has a carrier component, on which the at least one indicator is fixed and thus forms an assembly unit, which is arrangeable as a whole on or in the material of the material body. Reference can be made in this regard to all statements on the proposed hygiene device according to the first and second teaching.

According to a further teaching, which also has independent significance, a monitoring arrangement having a proposed hygiene device is disclosed. Reference can be made in this regard to all statements on the proposed hygiene device according to the first and second teaching.

It is essential according to the proposed monitoring arrangement that it has an evaluation unit having a receiver module associated with the transmitter module. The evaluation unit is thus capable of acquiring, reading out, evaluating, and/or further processing or the like the sensor data transmitted by the transmitter module. This monitoring arrangement thus permits a more flexible and strictly defined selection of the location for the readout of the sensor data and an accompanying check about the presence or absence of electromagnetic signals.

According to a particularly preferred embodiment, the proposed monitoring arrangement has a signal generator, which generates a signal if a previously defined threshold value for a parameter measured by the sensor is exceeded. The signal generator offers the advantage that the result of the sensor data is thus communicated outward without the necessity existing of evaluating the sensor data directly at the receiver module or the like. The monitoring arrangement can be arranged in a mobile or stationary manner, which is linked to a saving of installation space. This results in a high level of compactness, lower costs, and not least special flexibility with respect to the possible applications.

According to a further teaching, which also has independent significance, a return arrangement is disclosed for a proposed hygiene device, wherein the return arrangement has a receptacle unit, configured to receive a hygiene device, and a dispenser unit, configured to dispense a hygiene device. Such a return arrangement permits the disposal, for example, of respiratory masks in a particularly simple and environmentally friendly manner. Used respiratory masks are thus prevented from being disposed of in nature, the street, or in public.

According to one preferred embodiment, the return arrangement dispenses an unused hygiene device by means of the dispenser unit when a dispensing criterion has previously been met. This enables a particularly efficient supply with a proposed hygiene device and solves its disposal in a particularly simple manner. The return arrangement can be arranged in a mobile or stationary manner here, which offers a particular level of flexibility in its arrangement.

According to one preferred embodiment, the return arrangement has a monitoring arrangement. This enables the monitoring of the proposed hygiene device and its return in a particularly simple and compact manner.

According to a further teaching, which also has independent significance, a respiratory mask is disclosed, having a mask body, which covers the mouth and nose of a user in the intended applied state and in particular has multiple plies of material, having fixing elements fastened on the mask body, in particular fastening bands, configured for fixing the mask body on the head of the user, wherein the respiratory mask has at least one sensor for measuring a parameter. It is essential that the respiratory mask has at least one transmitter module on or in the material of the mask body, the at least one sensor is integrated in the transmitter module, and the transmitter module is designed for contactless transmission of sensor data of the at least one sensor and without its own electrical energy source.

In the following, the invention is explained in more detail on the basis of a drawing, which solely illustrates exemplary embodiments. In the figures of the drawing

The hygiene device has a material body covering a region, in particular of a person or an object, in the intended positioned state. The material body can consist here of one or multiple plies of material, in particular moisture absorption material. The moisture absorption material can be made of a plastic material, wood, paper, and/or granular material, such as sand or animal bedding. In addition, the hygiene device has at least one sensor for measuring a parameter.

It is essential in the proposed hygiene device that the hygiene device has at least one transmitter module 5 on or in the material of the material body, the at least one sensor 4 is integrated into the transmitter module 5, and the transmitter module 5 is designed for the contactless transmission of sensor data of the at least one sensor 4 and without its own electrical energy source.

The term "module" means here a group of components necessary for the intended function, which are functionally related. "Without its own electrical energy source" means here that no electrical component is present for providing useful energy, for example, a battery or an accumulator. The transmitter module 5 is designed as a passive electrical component. "Passive" means here that the intended function and the required energy for exerting the intended function have to be externally supplied. Components which store electrical energy statically in an electrical field, for example capacitors, can be present, in contrast.

The proposed hygiene device is explained hereinafter on the basis of a respiratory mask 1, which is to be understood solely as an exemplary embodiment and as nonrestrictive.

Figure 1:
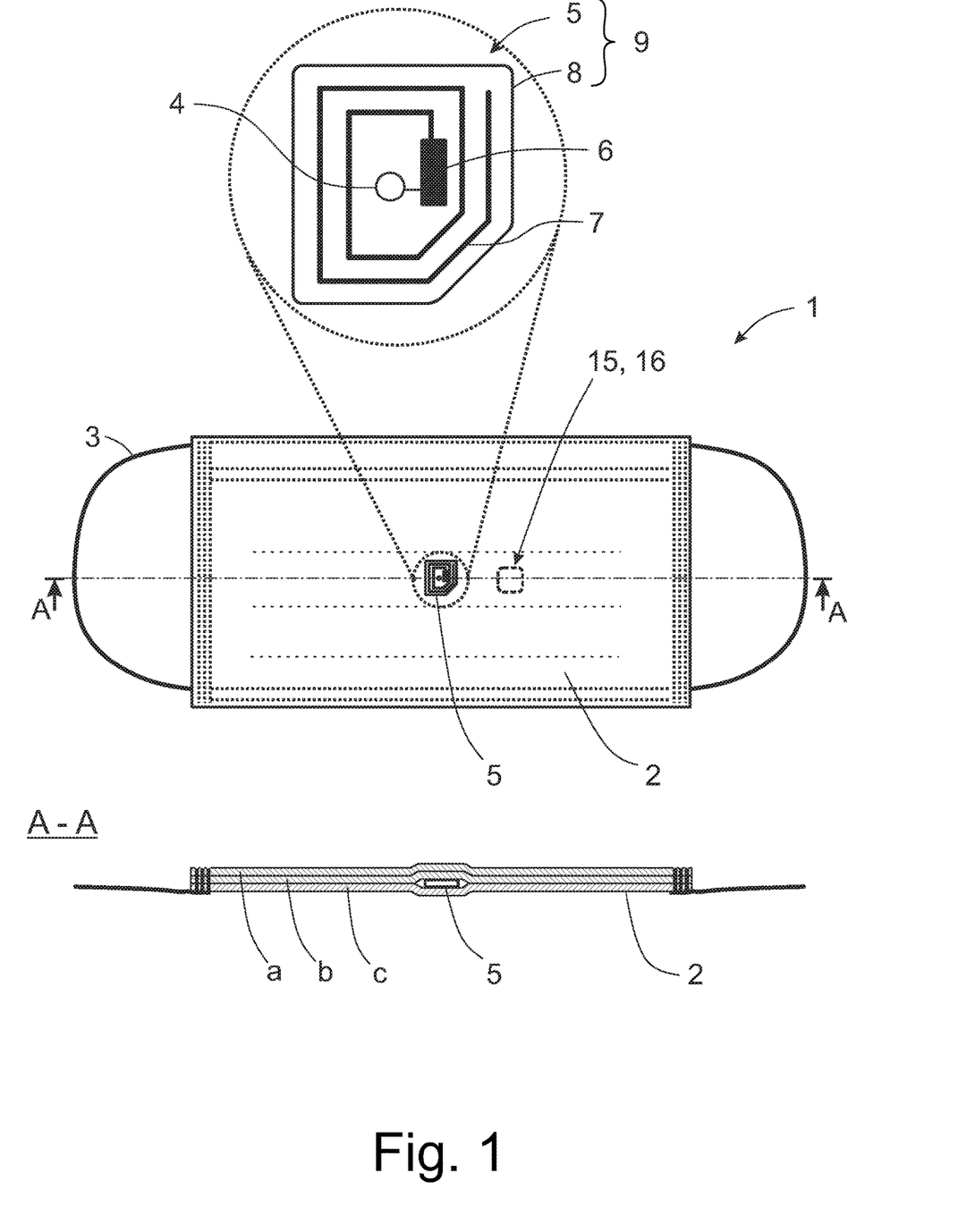
FIG. 1 shows a first exemplary embodiment of a proposed hygiene device in the form of a respiratory mask in a sectional and schematic illustration.

The respiratory mask 1 shown in FIG. 1, which forms the hygiene device, has a mask body 2 covering the mouth and nose of a user B in the intended applied state, which forms the material body. The mask body 2 can consist here of one or multiple plies a, b, c of material, in particular nonwoven material, fabric, or the like. Moreover, fixing elements 3, in particular fastening bands, are configured on the mask body 2 for fixing the mask body 2 on the head of the user B. Furthermore, the respiratory mask 1 has at least one sensor 4 for measuring at least one parameter.

It is to be emphasized once again that the proposed hygiene device can also be designed in another way, for example as an animal toilet device. The hygiene device then has, for example, a material body covering a region of an animal toilet in the intended positioned state.

The term "animal toilet" means here any type of underlay or container which is configured to absorb excretions which originate from animals, preferably from household pets, such as dogs, cats, hamsters, or rabbits.

The material body can have moisture absorption material here. In an animal toilet device, the moisture absorption material is made in particular of granular material. The moisture absorption material can be made in the case of the animal toilet device, but also in any other proposed hygiene device, from a plastic material, wood, paper, and/or granular material, in particular from animal bedding, sand, natural clay, or bentonite. The granular material can be enclosed at least in sections by packaging here, preferably for the purpose of its sterile packaging.

In addition, the proposed hygiene device has at least one sensor 4 for measuring a parameter in the granular material and/or on the packaging of the granular material.

Here and preferably, the at least one sensor 4 is configured to make a contamination state of the hygiene device based on the measured parameter derivable. Furthermore, the contamination state, here and preferably, is represented by a contamination class from a group of predefined contamination classes. The contamination state can be assigned to one of these contamination classes. Here and preferably, the predefined group of contamination classes exclusively includes the contamination classes "contaminated" and "non-contaminated". Alternatively, the predefined group of contamination classes can contain those which each represent a specific temperature, moisture, light, acceleration, vibration, and/or degree of contamination by microorganisms and/or viruses. Furthermore, it can be provided that the predefined group of contamination classes includes those which represent specific organisms, for example *Escherichia coli*.

The respiratory mask 1, which is set forth solely as an example of a proposed hygiene device, will be discussed once again in more detail hereinafter. It is essential in the proposed respiratory mask 1 that the respiratory mask 1 has at least one transmitter module 5 on or in the material of the mask body 2, the at least one sensor 4 is integrated into the transmitter module 5, and the transmitter module 5 is designed for the contactless transmission of sensor data of the at least one sensor 4 and without its own electrical energy source.

Figure 2:
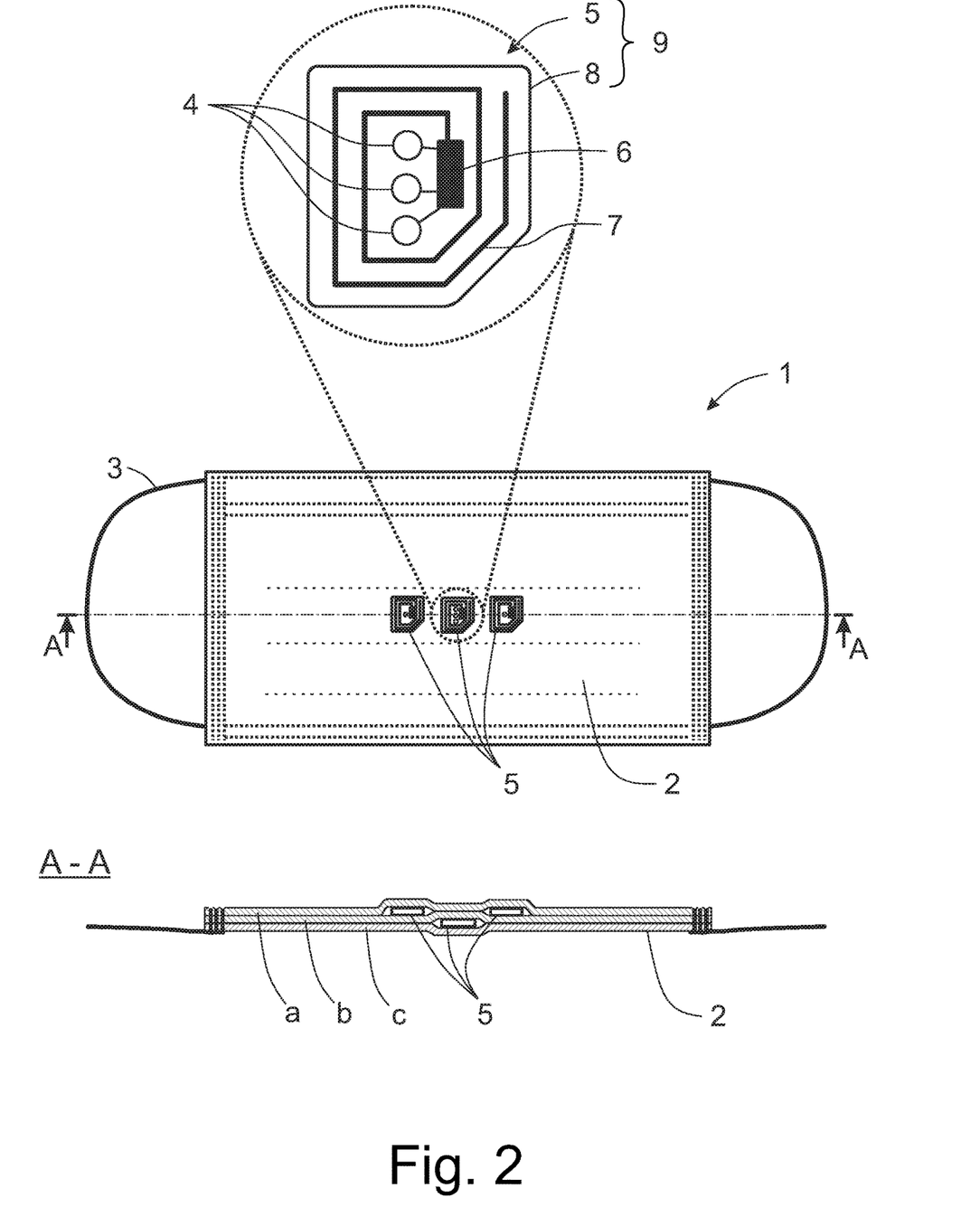
FIG. 2 shows a second exemplary embodiment of a proposed hygiene device in the form of a respiratory mask in a sectional and schematic illustration.

Here and preferably, as shown in FIGS. 1 and 2, the at least one transmitter module 5 is designed as an RFID and/or NFC module. RFID stands for "radio-frequency identification" and refers to a technology for transmitter-receiver systems for automatic and contactless identification and location of objects and living beings by means of radio waves. NFC stands for "near field communication" and is a transmission standard based on the RFID technology for the contactless exchange of data. As components required for the intended function, the RFID and/or NFC module here and preferably has at least one sensor 4, at least one microchip 6 for converting the parameters measured by the sensor 4 into an RFID- and/or NFC-compatible code, and at least one antenna 7 for transmitting the sensor data. The respiratory mask 1 can preferably have one or multiple transmitter modules 5, which are exclusively designed as RFID modules, or one or multiple transmitter modules 5, which are exclusively designed as NFC modules, or both types of transmitter modules 5.

Here and preferably, the at least one transmitter module 5 is designed to be wireless. "Wireless" means here the absence at least of connecting cables and, preferably, the absence of any flexible single-wire or multi-wire composite of individual conductor elements jacketed with insulating materials, which is used for transmitting energy or information. This is enabled by the compact design of the transmitter module 5 as an RFID and/or NFC module and permits a saving in installation space and material.

All illustrated, preferred embodiments are made so that the at least one transmitter module 5 has an in particular plate-shaped or film-shaped carrier component 8, on which the sensor 4 and at least one further component of the transmitter module 5 required for the intended function are fixed relative to one another and thus form an assembly unit 9, which is arranged as a whole on or in the material of the mask body 2. The carrier component 8 can consist in this case of metal or plastic, here and preferably of a sticker, or the like.

Furthermore, the transmitter module 5 is integrated fixed in place between two material plies a, b of the mask body 2 and/or is fastened on the outside and/or the inside of the mask body 2. The fastening can be carried out by adhesive bonding, sewing, or the like. In principle, the mask body 2 can consist of one material ply a. Here and preferably, the mask body 2 has at least two, preferably at least three material plies a, b, c. No additional aids, for example, holders, cords, bands, or the like, are thus necessary for the fastening of the transmitter module 5, since it can be arranged between the material plies a, b, c, and it moreover prevents a nondestructive detachment of the transmitter module 5 from the mask body 2. The transmitter module 5 is thus fastened captively on or in the mask body 2, in particular on the outside and/or on the inside of the mask body, due to which mask body 2 and transmitter module 5 form a cohesive unit. Alternatively, the at least one transmitter module 5 can be arranged loosely on the mask body 2.

The respiratory mask 1 can have, as FIG. 1 illustrates, precisely one transmitter module 5 having precisely one sensor 4 or multiple sensors 4 or, as FIG. 2 illustrates, multiple transmitter modules 5 each having precisely one sensor 4 or each having multiple sensors 4. In the case of an embodiment having multiple transmitter modules 5, these are preferably fastened spaced apart from one another. In the case of an embodiment having multiple sensors 4, these can either be structurally identical or different here. Either the same parameter can thus be measured multiple times at different points of the mask body 2 or multiple different parameters can be measured.

Here and preferably, the at least one sensor 4 of the at least one transmitter module 5 can measure at least one parameter, including, but not restricted to, temperature, moisture, ambient humidity, light, optical density, acceleration, vibration, and degree of contamination by microorganisms and/or viruses. The parameter or parameters measured by the sensor 4 are based here on the measurement of parameters from the environment and/or on the measurement of parameters which originate from the respective respiratory mask user B. The large number of the measurable parameters enables a particular flexibility with respect to the application here, wherein the parameters measured by the sensor 4 permit inferences here about the environment of the respiratory mask 1 and/or about the respective respiratory mask user B. In addition, the evaluation of at least one of these parameters or a combination of several of these parameters finally permits statements with respect to the contamination and/or wearing time of the respective respiratory mask 1 as such by the respiratory mask user B.

Here and preferably, the respiratory mask 1 is designed as a single-use or multiple-use product. As a single-use product, the respiratory mask 1 is disposed as such after the proper use and not reused. As a multiple-use product, the mask body 2 can be made from a higher-quality and/or reusable material and the transmitter module 5 fastened on or in the mask body 2 can be designed more complexly, so that a repeated use and possibly a higher electronic complexity of the respiratory mask 1 can be provided.

Here and preferably, a corresponding receiver module 10, preferably an RFID and/or NFC transmitter, for acquiring the transmitted sensor data is associated with the transmitter module 5 of the proposed respiratory mask 1. The receiver module 10 is provided spatially separated from the mask body 2 or from the respiratory mask 1 as such. Therefore, transmitter module 5 and receiver module 10 jointly result in an interacting transmitter-receiver system 11, preferably an RFID and/or NFC system. Here and preferably, an electromagnetic field can become active starting from the corresponding receiver module 10, in which the transmitter module 5 is activated and externally supplied with energy via the antenna. The proposed respiratory mask 1 can thus be designed without its own energy source and can thus additionally be used in environments having devices sensitive to electromagnetic signals, for example, hospitals, clinics, senior homes, universities, research institutes, aircraft, or the like.

It is particularly to be emphasized that, here and preferably, the interaction of the transmitter-receiver system 11 required for the intended function can be carried out up to a range of at least 3 m, preferably at least 5 m, more preferably at least 7 m.

According to a further teaching, which has independent significance, a proposed hygiene device, in particular a respiratory mask 1, in particular according to the above teaching, is disclosed, having a material body, which covers a region in the intended positioned state, and in particular has multiple plies a, b, c of material, in particular moisture absorption material, which is made of a plastic material, wood, paper, and/or granular material, in particular a mask body 2, wherein the proposed hygiene device, in particular respiratory mask 1, has at least one pH and/or moisture indicator 15 on or in the material of the material body, in particular mask body 2, as schematically shown by dashed lines in FIG. 1. Reference can thus be made to all statements on the proposed hygiene device according to the first teaching.

Here and preferably, as also schematically shown by dashed lines in FIG. 1, it is provided that the sensor 4 and/or the indicator 15 is covered by a buffer arrangement 16, in particular on the side facing toward the respiratory mask user B and/or on the side facing away from the respiratory mask user B. This is configured to absorb moisture and deliver it with a time delay to the sensor 4 and/or indicator 15. Here and preferably, the buffer arrangement 16 has a material layer which is configured to absorb moisture and deliver it with a time delay to the sensor 4 and/or indicator 15. Here and preferably, the buffer arrangement 16 has salts and/or other materials and/or plastics and/or a membrane or the like or a combination thereof. These enable moisture to be absorbed from the environment and delivered homogeneously to the at least one sensor 4. Variations of the measured parameters or the indication provided by the indicator can thus be minimized, which could otherwise arise due to continuous inhalation and exhalation of the respiratory mask user B in the intended positioned state of the respiratory mask 1. It can be provided here that the material layer is arranged in a chamber. The chamber can be a housing which encloses the sensor 4 and/or indicator 15.

According to a further teaching, which also has independent significance, a transmitter module 5 for a proposed hygiene device, in particular respiratory mask 1, is disclosed, wherein the transmitter module 5 has a carrier component 8, on which the at least one sensor 4 and at least one further component of the transmitter module 5 required for the intended function, preferably the microchip 6 and/or the antenna 7, more preferably all components required for the intended function of the at least one transmitter module 5 are fixed relative to one another and thus form an assembly unit 9, which is arrangeable as a whole on or in the material of the material body, in particular mask body 2. This transmitter module 5 can have a housing, in particular the above-described housing. The assembly unit 9 can be attached, in particular adhesively bonded, if needed on a respiratory mask 1, which up to this point has not had a transmitter module 5. Reference can be made in this regard to all statements on the proposed hygiene device 1 according to the first teaching and to the further teaching.

According to a further teaching, which also has independent significance, an indicator module for a proposed hygiene device, in particular respiratory mask 1, is disclosed, wherein the indicator module has a carrier component 8, on which the at least one indicator 15 is fixed and thus forms an assembly unit 9, which is arrangeable as a whole on or in the material of the material body, in particular mask body 2. This indicator module can have a housing, in particular the above-described housing. The assembly unit 9 can be attached, in particular adhesively bonded, if needed on a respiratory mask 1, which up to this point has not had an indicator module. Reference can be made in this regard to all statements on the proposed hygiene device 1 according to the first teaching and to the further teachings.

Figure 3:
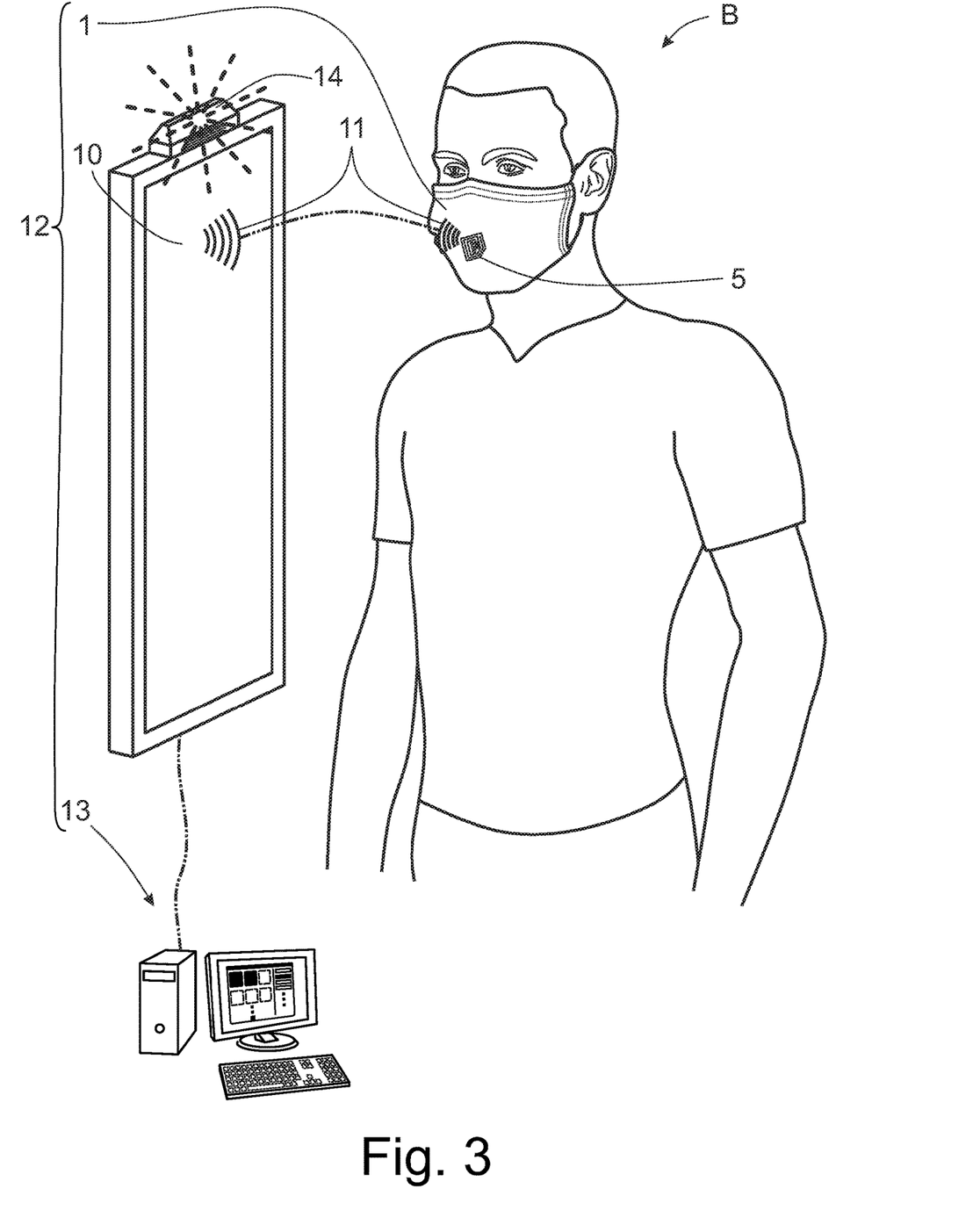
FIG. 3 shows the proposed hygiene device in the form of a respiratory mask according to FIG. 1 in the intended applied state having a proposed monitoring arrangement in a schematic overview illustration.

According to a further teaching, which has independent significance, as shown in FIG. 3, a monitoring arrangement 12 having an above-proposed hygiene device, in particular respiratory mask 1, is provided, which has an evaluation unit 13 and a receiver module 10 associated with the at least one transmitter module 5 of the hygiene device, wherein the evaluation unit 13 acquires and/or reads out and then evaluates and/or further processes the sensor data transmitted by the transmitter module 5 by means of the receiver module 10. The receiver module 10 associated with the transmitter module 5 of the respiratory mask 1, which acquires and subsequently evaluates and/or further processes the data transmitted by the transmitter module 5, is here and preferably part of the evaluation unit 13. "Evaluating" means here checking the acquired data with regard to their meaning and/or importance in order to make them usable. "Further processing" means here in particular displaying, storing, converting, processing, and/or relaying or the like. Alternatively, the receiver module 10 can be provided spatially separated from the evaluation unit 13. The evaluation unit 13 can here and preferably be designed as a computer, server, cloud application, mobile app, tablet, or smart phone. In addition, it can be provided that the evaluation unit 13 is arranged outside the space or the building or the like in which the other components of the monitoring arrangement 12 are located. Reference can be made in this regard to all statements on the proposed hygiene device 1 according to the first teaching and to the further teachings.

The proposed monitoring arrangement 12 preferably has a signal generator 14, so that if a previously defined threshold value for at least one parameter measured by the at least one sensor 4 is exceeded, it generates a signal. The signal can be tactile, acoustic, visual, olfactory, or the like here. Additionally or alternatively, the signal generator 14 can initiate an information chain as the signal, for example, the display of the measured sensor data and/or the listing of the previously measured sensor data and/or the sending of a message, preferably an email, or the like. It can also be provided that following such an information chain, one or multiple of the abovementioned signals are additionally generated. The signal generator 14 can be captively connected to the evaluation unit 13 or can be designed as an independent component detached from the evaluation unit 13.

The monitoring arrangement 12 can be arranged in a mobile or stationary manner. This makes it clear that the proposed solution is applicable to greatly varying spatial and hygienic boundary conditions, without having to accept any functional losses of the proposed respiratory mask 1 or due to the proposed respiratory mask 1. A mobile embodiment of the monitoring arrangement 12 as such and also its components required for the intended function is thus preferably also possible. This mobile embodiment enables the flexible use of the proposed respiratory mask 1 and the proposed monitoring arrangement 12 even at locations which are poorly developed with respect to technology and/or infrastructure, for example, crisis regions and/or developing countries or the like.

According to a further teaching, which has independent significance, a return arrangement is provided for an above proposed hygiene device, in particular respiratory mask 1. This has a receptacle unit, configured to receive a preferably used proposed hygiene device, in particular respiratory mask 1. In addition, it has a dispenser unit, configured to dispense a preferably unused proposed hygiene device, in particular respiratory mask 1. Reference can be made in this regard to all statements on the proposed hygiene device 1 according to the first teaching and to the further teachings.

Here and preferably, the return arrangement dispenses an unused proposed hygiene device, in particular respiratory mask 1, by means of the dispenser unit if a dispensing criterion was met beforehand, preferably immediately. Such a dispensing criterion is, here and preferably, the receiving of a preferably used proposed hygiene device, in particular respiratory mask 1, by the receptacle unit.

The return arrangement can be arranged in a mobile or stationary manner. Here and preferably, the return arrangement has an above proposed monitoring arrangement. This again makes it clear that the proposed solution is applicable to greatly varying spatial and hygienic boundary conditions. This preferred embodiment enables the flexible use of the proposed hygiene device, in particular respiratory mask 1, by a combination of the proposed return arrangement and the proposed monitoring arrangement 12, and opens up the option of monitoring and returning in a particularly simple manner, in particular at space-restricted and/or strongly frequented locations, such as entry regions of hospitals, clinics, or supermarkets.

According to a further teaching, which has independent significance, a respiratory mask 1 is provided, having a mask body 2, which covers the mouth and nose of a user B in the intended applied state, and in particular has multiple plies a, b, c of material, having fixing elements 3 fastened on the mask body 2, in particular fastening bands, configured for fixing the mask body 2 on the head of the user B, wherein the respiratory mask 1 has at least one sensor 4 for measuring a parameter. It is essential that the respiratory mask 1 has at least one transmitter module 5 on or in the material of the mask body 2, the at least one sensor 4 is integrated into the transmitter module 5, and the transmitter module 5 is designed for the contactless transmission of sensor data of the at least one sensor 4 and without its own electrical energy source. Reference can be made in this regard to all statements on the proposed hygiene device 1 according to the first teaching and to the further teachings.

The invention claimed is:

1. A monitoring arrangement comprising:
    a hygiene device comprising
        a material body configured to cover a region in an intended positioned state, said material body comprising one single ply or multiple plies of material, and
        at least one sensor configured to measure a parameter, said parameter being a degree of contamination by microorganisms and/or viruses, said sensor being integrated in at least one transmitter module disposed on or in the material of the material body, said transmitter module being configured for contactless transmission of sensor data derived from the measured parameter of the at least one sensor without having its own electrical energy source;
    a receiver module configured to acquire the transmitted sensor data associated with the transmitter module of the hygiene device, said transmitter module and said receiver module jointly forming an interacting transmitter-receiver system having a range of at least 5 m; and
    an evaluation unit configured to acquire and/or read out and then evaluate and/or further process the sensor data transmitted by the transmitter module by means of the receiver module;
    wherein the hygiene device has at least one pH and/or moisture indicator on or in the material of the material body, and
    wherein the sensor and/or the indicator is covered by a buffer arrangement, which is configured to absorb moisture and deliver it with a time delay to the sensor and/or indicator.

2. The monitoring arrangement as claimed in claim 1, wherein the hygiene device is a respiratory mask, wherein the material body is a mask body, wherein the region the mask body covers in the intended positioned state is a user's mouth and nose, wherein the hygiene device further comprises fixing elements for fixing the mask body on the user's head, and wherein the transmitter module is disposed on or in the mask body.

3. The monitoring arrangement as claimed in claim 2, wherein the parameter measured by the at least one sensor is based on measurements of an environmental parameter and/or on measurements of a parameter of the user.

4. The monitoring arrangement as claimed in claim 2, wherein the fixing elements are fastening bands fastened on the mask body configured for fixing the mask body on the user's head.

5. The monitoring arrangement as claimed in claim 1, wherein the hygiene device is an animal toilet device, wherein the region the material body covers in the intended position state is an animal toilet, wherein the single ply or at least one of the multiple plies of the material body comprises a moisture absorption material, wherein the moisture absorption material is made of granular material, wherein the granular material is optionally enclosed at least in sections by a packaging, and wherein the transmitter module is disposed in the granular material and/or on the packaging of the granular material.

6. The monitoring arrangement as claimed in claim 1, wherein the at least one sensor is configured to determine a contamination state of the hygiene device based on the measured parameter.

7. The monitoring arrangement as claimed in claim 1, wherein the transmitter module is an RFID and/or NFC module, which includes the at least one sensor, a microchip for converting the parameter measured by the sensor into an RFID- and/or NFC-compatible code, and at least one antenna for transmitting the sensor data.

8. The monitoring arrangement as claimed in claim 7, wherein the transmitter module has a plate-shaped or film-shaped carrier component on which the at least one sensor and the microchip and/or the antenna are fixed relative to one another and thus form an assembly unit, which is arranged as a whole on or in the material of the material body.

9. The monitoring arrangement as claimed in claim 1, wherein the transmitter module is wireless.

10. The monitoring arrangement as claimed in claim 1, wherein the transmitter module is fixed in place between two material plies of the material body and/or is fastened on an outside and/or on an inside of the material body, and/or the transmitter module is arranged loosely on or in the material body.

11. The monitoring arrangement as claimed in claim 1, wherein the transmitter module is captively fastened on or in the material body, and wherein the transmitter module is detachable from the material body destructively or nondestructively.

12. The monitoring arrangement as claimed in claim 1, wherein the hygiene device has one of (a), (b), (c) and (d) below:
    (a) precisely one transmitter module having precisely one sensor;
    (b) precisely one transmitter module having multiple sensors;
    (c) multiple transmitter modules each having precisely one sensor; and
    (d) multiple transmitter modules each having multiple sensors.

13. The monitoring arrangement as claimed in claim 1, wherein the at least one sensor of the transmitter module is configured to measure one or more further parameters selected from the group consisting of temperature, moisture, light, acceleration, and vibration.

14. The monitoring arrangement as claimed in claim 1, wherein the hygiene device is a single-use device.

15. The monitoring arrangement as claimed in claim 1, wherein the transmitter module is configured to be activated and supplied with energy exclusively by the receiver module.

16. The monitoring arrangement as claimed in claim 1, wherein the transmitter module comprises a carrier component on which at least one sensor and at least one further component of the transmitter module are fixed relative to one another and thus form an assembly unit, which is arrangeable as a whole on or in material of the material body of the hygiene device.

17. The monitoring arrangement as claimed in claim 1, wherein the monitoring arrangement includes a signal generator, wherein the signal generator is configured to generate a signal when a previously defined threshold value for the parameter measured by the sensor is exceeded.

18. The monitoring arrangement as claimed in claim 1, wherein the monitoring arrangement is arranged in a mobile or stationary manner.

19. The monitoring arrangement as claimed in claim 1, wherein the interacting transmitter-receiver system has a range of at least 7 m.

20. An indicator module for a hygiene device, said hygiene device comprising:
- a material body configured to cover a region in an intended positioned state, said material body comprising one single ply or multiple plies of material; and
- at least one sensor configured to measure a parameter, said parameter being a degree of contamination by microorganisms and/or viruses, said sensor being integrated in at least one transmitter module disposed on or in the material of the material body, said transmitter module being configured for contactless transmission of sensor data derived from the measured parameter of the at least one sensor without having its own electrical energy source;
- wherein the indicator module comprises a carrier component on which at least one indicator is fixed and thus forms an assembly unit, which is arrangeable as a whole on or in the material of the material body,
- wherein the hygiene device has at least one pH and/or moisture indicator on or in the material of the material body, and
- wherein the sensor and/or the indicator is covered by a buffer arrangement, which is configured to absorb moisture and deliver it with a time delay to the sensor and/or indicator.

21. A return arrangement for a hygiene device, said hygiene device comprising:
- a material body configured to cover a region in an intended positioned state, said material body comprising one single ply or multiple plies of material; and
- at least one sensor configured to measure a parameter, said parameter being a degree of contamination by microorganisms and/or viruses, said sensor being integrated in at least one transmitter module disposed on or in the material of the material body, said transmitter module being configured for contactless transmission of sensor data derived from the measured parameter of the at least one sensor without having its own electrical energy source;
- wherein the return arrangement has a receptacle unit configured for receiving the hygiene device after use, and a dispensing unit configured for dispensing an unused hygiene device,
- wherein the return arrangement is configured to dispense the unused hygiene device by means of the dispensing unit when a dispensing criterion is met,
- wherein the dispensing criterion is receipt of a used hygiene device by the receptacle unit,
- wherein the return arrangement further comprises a monitoring arrangement that includes an evaluation unit and a receiver module associated with the transmitter module of the hygiene device, and
- wherein the evaluation unit is configured to acquire and/or read out and then evaluate and/or further process the sensor data transmitted by the transmitter module by means of the receiver module.

22. The return arrangement as claimed in claim 21, wherein the return arrangement is arranged in a mobile or stationary manner.

\* \* \* \* \*